United States Patent [19]
Wakamatsu

[11] Patent Number: 5,680,051
[45] Date of Patent: Oct. 21, 1997

[54] ELECTROMAGNETIC INDUCTION-TYPE PROBE

[75] Inventor: Hideki Wakamatsu, Hyogo, Japan

[73] Assignee: Hewlett-Packard Company, Palo Alto, Calif.

[21] Appl. No.: 579,318

[22] Filed: Dec. 27, 1995

[30] Foreign Application Priority Data

Dec. 29, 1994 [JP] Japan ..................... 6-338615

[51] Int. Cl.$^6$ .................................. G01N 27/02
[52] U.S. Cl. ............................ 324/445; 324/439
[58] Field of Search ....................... 324/439, 445, 324/450

[56] References Cited

U.S. PATENT DOCUMENTS

| | | |
|---|---|---|
| 3,030,573 | 4/1962 | Yamashita et al. ............ 324/445 |
| 3,292,077 | 12/1966 | Sloughter ...................... 324/445 |
| 3,867,688 | 2/1975 | Koski ............................ 324/445 |
| 4,220,920 | 9/1980 | Gross ............................ 324/445 |
| 5,157,332 | 10/1992 | Reese ............................ 324/445 |
| 5,252,925 | 10/1993 | Matsumoto et al. .......... 324/445 |
| 5,268,642 | 12/1993 | Uchidomi ..................... 324/445 |
| 5,341,102 | 8/1994 | Akiyama et al. .............. 324/445 |

FOREIGN PATENT DOCUMENTS 6-172023  6/1994  Japan.
0741138   6/1980  U.S.S.R. ................ 324/445

OTHER PUBLICATIONS

Resmar et al., "A Miniture Conductivity Meter", Australian Journal of Instrumentation and Control, vol. 31, No. 1, pp. 5–8, Feb. 1975.

Primary Examiner—Ernest F. Karlsen
Assistant Examiner—Diep Do

[57] ABSTRACT

An electromagnetic induction-type probe, for measuring the electrical properties of a solution, exhibits both a reduced size and a wide band property. The probe includes a primary transformer, composed of a toroidal core with a primary coil winding, a secondary transformer composed of a toroidal core with a secondary, coil winding, an electrostatic shield and coaxial cables which connect the probe and the main frame of a measuring instrument. The structure of the probe is symmetrical in order to eliminate measurement errors due to the asymmetry of the electrical field produced in the solution. The symmetry of the electrical field in the solution is maintained up to the high-frequency region and a wideband effectiveness is realized by connecting the center tap terminal of a balancer to the outer conductors of the coaxial cables and the other terminals of the balancer to both ends of the gap of the electrostatic shield. Since the balancer can be contained in the handle of the probe, the size of the probe is reduced.

3 Claims, 4 Drawing Sheets

5,680,051

ELECTROMAGNETIC INDUCTION-TYPE PROBE

FIELD OF THE INVENTION

This invention concerns, in general, an impedance measurement device; and in particular, it concerns an electromagnetic induction-type probe which is used for measuring electrical properties, testing, and control of the structures of colloidal substances.

BACKGROUND OF THE ART

Colloids are disperse systems consisting of fine particles of dispersoid and a continuous-phase dispersion medium; the dispersoid substance and the dispersion medium are not uniformly mixed. As a method for evaluating the form of this kind of non-uniform structure, its electrical properties are measured, i.e., conductivity, permittivity, etc. In recent years, methods for measuring permittivity using impedance measurements have been studied.

Applicant has proposed an electromagnetic induction-type conductivity and permittivity meter as an effective means for measuring the capacitance of solutions with large conductivities, i.e., their permittivities, in Japanese Patent Application No. 6[1994]-172023. This device solves the problem of errors due to electrode polarization, which is a disadvantage of prior art electrode types, and is able to perform accurate measurements of permittivity, while avoiding conductivity effects. In that Application, a probe structure and a simple correction method were proposed. The present invention comprises a probe with improved structural elements and provides for both a wide band property and a smaller size.

In Japanese Patent Application No. 6[1994]-172023, an electromagnetic induction-type probe is disclosed wherein the electrical field is made symmetrical with respect to a plane passing through the centers of the rings of the annular transformers and perpendicular to the central axis of the rings. FIGS. 3 and 4 hereof show structures that were exhibited as examples of this device.

An outline of the operation of these structures is as follows. An alternating current signal from signal source 2 in main frame 1 of the impedance measuring instrument is applied to primary coil 11 of an electromagnetic induction-type probe 8, and primary toroidal core 10 is excited. As a result, an induced current flows in the solution into which the probe has been dipped. This current is linked with secondary toroidal core 12, and a magnetic flux is excited in this core. The current in secondary coil 13 induced by this magnetic flux is measured by ammeter 5 in main frame 1 of the impedance measuring instrument. The applied signal voltage is measured by voltmeter 4, and the impedance of the solution is obtained from the ratio between the measured value of the voltmeter and the measured value of the ammeter. The conductance is obtained from the resistance component of the measured value of the impedance, and the permittivity is obtained from the capacitive component by calculation processing. Furthermore, in FIGS. 3 and 4, 3 is the resistance, and 9 is the outer resin mold of the electromagnetic induction-type probe.

FIGS. 3 and 4 are structures in which the toroidal cores of the primary and secondary transformers are arranged concentrically. Since the centers of the rings of the two toroidal cores and the central axes of these rings coincide, a symmetrical structure is formed with respect to a plane passing through the center and perpendicular to the central axis. In FIG. 3, the structure of the cores and the shield satisfies this condition of symmetry. The asymmetrical non-uniformity due to the fact that the current output points of coaxial cables 6 and 7 come from the sides of the respective cores, is equilibrated by compensating with the balun 18 and shunt 17. The equivalent circuit of the balun 18 is shown at 19. By this method, for example, there is a limit to measuring in a wide band of about 100 kHz to 30 MHz. A good equilibrium is obtained in the high-frequency band, but the excitation impedance is lowered in the low-frequency band, and the equilibrium is poor. Reducing the excitation impedance not only adversely affects the equilibrium, but also produces a magnetic flux outside the core of the balun. This magnetic flux causes a current to flow in a loop comprised of coaxial cable 6, shunt 17, coaxial cable 7, and shield 14. As a result, isolation between the primary and secondary transformers is adversely affected and the measurement error is increased.

In order to prevent the reduction of the excitation impedance in the lower frequencies, the number of windings must be increased, and therefore the annular core of the balun must be made larger. Since the coaxial cables are wound around this core, the outer form of the balun is continuously enlarged.

FIG. 2 shows an example of the outer appearance and dimensions of a practical electromagnetic induction-type probe. The probe is covered with a synthetic resin, and the two transformers are contained in the transformer part of the figure. The location of the balun is in the part of the handle close to the transformer part. However, it is not possible to enclose the balun in the handle part with the dimensions shown in the figure. If one tries to force the balun into the handle part, the shape of the handle part becomes complex, and not only is the attractiveness of the handle part adversely affected, but problems such as the limitation of the size of the solution container, the center of weight of the probe, the method of holding it, the question of washing it, etc., arise.

On the other hand, in the structure of FIG. 4, symmetry is obtained by passing the output wires of inner coil 13 to the outside through a hole 16, which is arranged in the radial direction of the ring and passes through the center of the cross section of outer core 10. Therefore, a balun is not needed, and the probe can be made smaller. However, as the permittivity of the core is reduced (this reduction being produced by the increase in the frequency), the problem arises that the symmetry of the electrical field is insufficient. The result is that the various capacitive couplings between the winding wires, cores, and shield can no longer be ignored, with respect to the inductance of the winding wires of the transformers. As a result, when the device is mass-produced, it becomes extremely difficult to obtain a structure and wiring wherein variations in the symmetry of the electrical field are so small that they can be ignored.

Thus, with the structure of FIG. 3, the probe must be made larger in order to measure the low-frequency band with better accuracy. Further, with the structure of FIG. 4, it is difficult to manufacture a probe with no variation in the high-frequency region. Thus, in this prior art technology, there is the problem that a small probe with a wide band cannot be realized.

This invention has the purpose of solving the aforementioned problems by providing an electromagnetic induction-type probe that has both wide-band properties and capacity for miniaturization.

SUMMARY OF THE INVENTION

An electromagnetic induction-type probe exhibits wide-band accuracy and a reduction in size by making use of the characteristics of the structure of FIG. 4, which enable a reduction in the size of the device, and add a means for correcting the asymmetry of the electrical field in the high-frequency region. A transformer with a center tap is the device which preserves the symmetry of the electrical field at high frequencies.

EXPLANATION OF SYMBOLS

1: Impedance measuring instrument main frame;
2: Signal source;
3: Resistance;
4: Voltmeter;
5: Ammeter;
6: Coaxial cable;
7: Coaxial cable;
8: Electromagnetic induction-type probe;
9: Outer resin molding;
10: Primary toroidal core;
11: Primary coil;
12: Secondary toroidal core;
13: Secondary coil;
14: Shield;
15: Gap;
16: Hole running through core;
17: Shunt;
18: Balun;
19: Equivalent circuit of balun;
31: Balancer;
32: Equivalent circuit of balancer;
a, b, c: Balancer terminals;

DETAILED DESCRIPTION OF THE INVENTION

Figure 1:
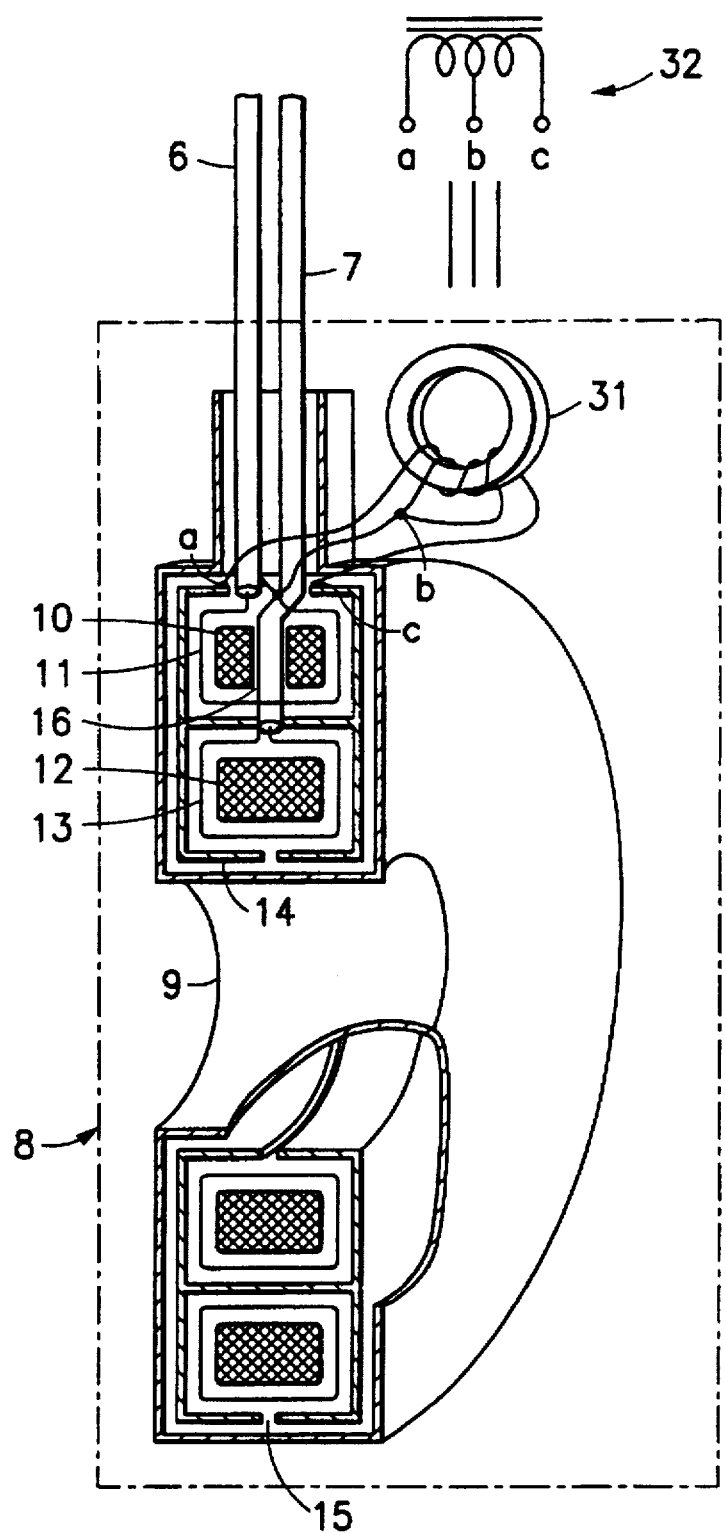
FIG. 1 is a diagram showing an actual example of this invention.
Figure 4:
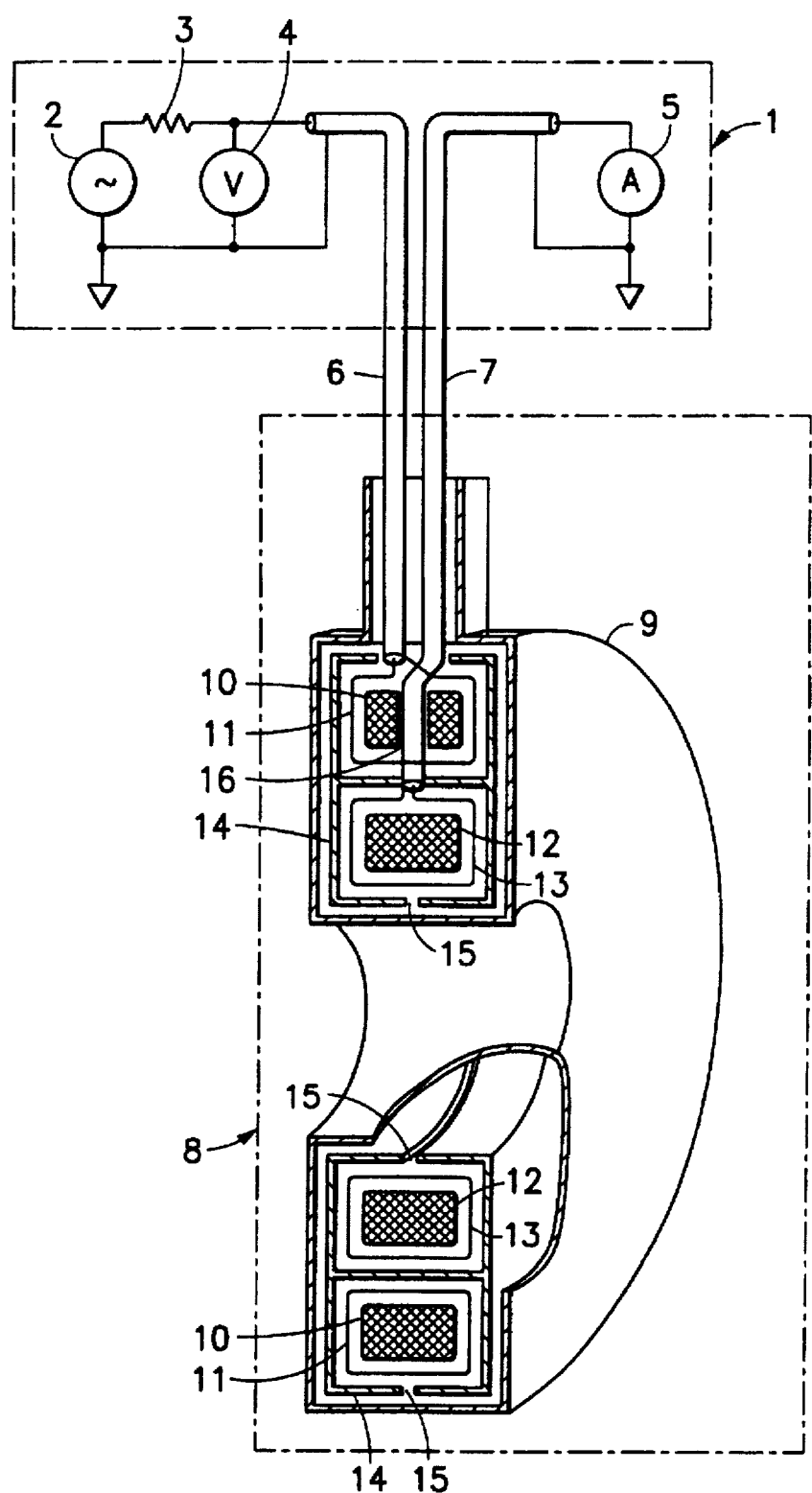
FIG. 4 is a diagram showing a second example of prior art technology.

An example of this invention is shown in FIG. 1. A balancer 31 is added to a probe having the symmetrical structure of the prior art technology, as a means for correcting the asymmetry of the electrical field in the high-frequency region. In this figure, the same numbers are given to the constituent elements with the same functions as in the prior art technology. The structure, aside from balancer 31, is the same as that in FIG. 4. However, the main frame of impedance measurement instrument 1 shown in FIG. 4 is omitted.

Balancer 31 may have any structure that is desired, as long as it is a transformer with a center tap, with an equivalent circuit as shown at 32 in the figure. A preferred structure, exhibiting small magnetic flux leakage, consists of a toroidal core on which are wound two coils with the same number of windings, the two conductive wires being insulated from each other, as shown at 31. The beginning of the winding of the primary coil is terminal a; terminal b is where the end of the winding of the primary coil and the beginning of the winding of the secondary coil are connected; and the end of the winding of the secondary coil is terminal c. Therefore, looking at terminals a and c from terminal b, potentials with opposite phases but the same amplitude appear. Terminal a of this balancer 31 is connected to 1 terminal of gap 15 of shield 14, and terminal c of the balancer is connected to the other terminal of gap 15; terminal b is connected to the outer conductor of input/output coaxial cables 6 and 7. These connection locations are very close to the current source points where the input/output terminals of primary coil 11 and secondary coil 13 and the coaxial cables are connected.

The asymmetrical part of the aforementioned electrical field is corrected by balancer 31, which is a transformer with a center tap. That is, since the potentials of the left and right ends of the shield, the current source points for the coaxial cables, are connected to terminals a and b of the balancer, they are excited with opposite phases and the same amplitudes with respect to the outer conductor of the current source point of the coaxial cables. That is, the mean value of the potentials of both ends of the gap of the shield is equal to the potential of the outer conductor of the current source point of the coaxial cables. Therefore, a symmetrical electrical field is generated outside the probe, and the potential of the coaxial cable current source point agrees with the mean potential of the solution; the current that flows from the probe to the solution in the capacitive coupling is not linked with the secondary transformer.

Figure 2:
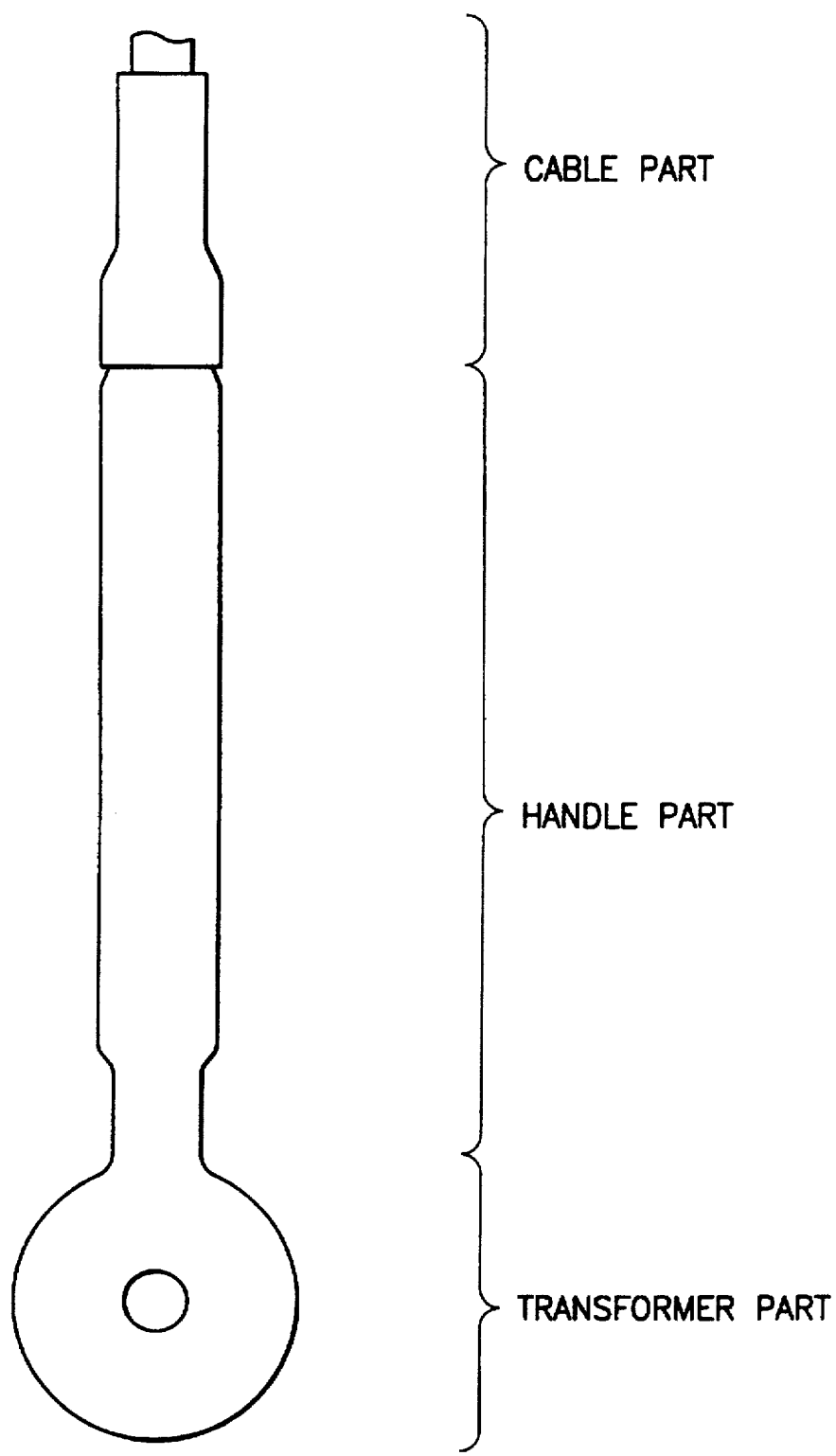
FIG. 2 is a diagram showing an example of the outer appearance of an electromagnetic induction-type probe.
Figure 3:
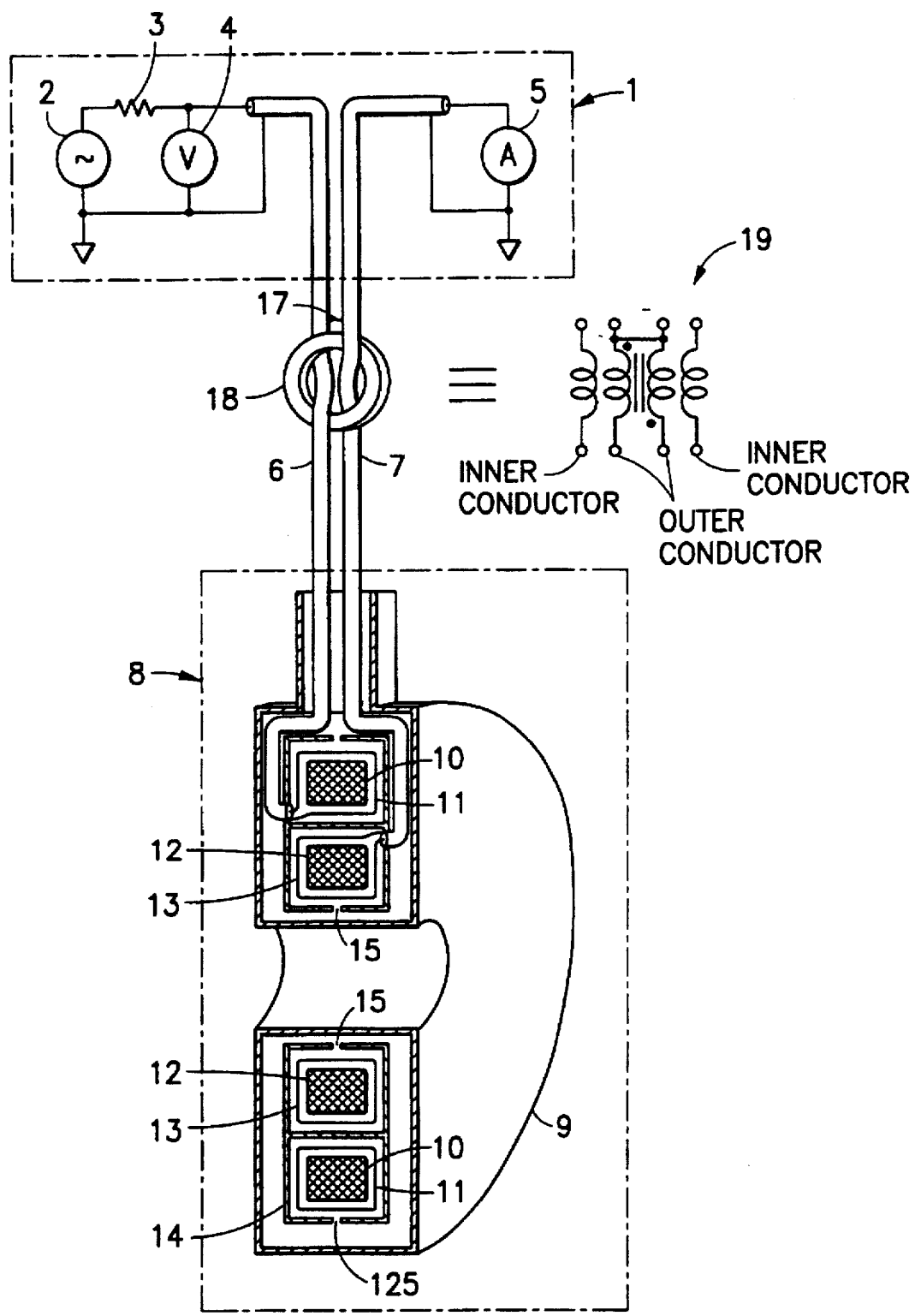
FIG. 3 is a diagram showing a first example of prior art technology.

The excitation impedance of balancer 31 must be high over the whole band, like balun 18 of FIG. 3, but since the winding wire of the balancer 31 need not be a coaxial cable, it can be made 1/10 the size of the balun needed in FIG. 3. As a result, it is easy to incorporate it into the handle part of the probe, formed as shown in FIG. 2.

An example of this invention is shown above, but this invention is not limited to the style, forms of parts, arrangement of parts, or other aspects shown in the example. If desired, modifications in the make-up of the invention are allowed, as long as they do not conflict with its essence.

EFFECTIVENESS OF INVENTION

If the balancer of this invention is added to the electromagnetic induction-type probe proposed in Japanese Patent Application No. 6[1994]-172023, a probe results with a narrow frame, which is easily handled, and with a wide frequency band.

I claim:

1. An electromagnetic induction-type probe for measuring electrical properties of solutions, comprising:

a primary transformer and a secondary transformer, one of said transformers having a large ring core and another of said transformers having a small ring core, said large ring core and small ring core placed concentrically, so that a center of each said core and a central axis of each thereof coincide;

electrostatic shield means positioned about said primary transformer and secondary transformer, and symmetrically arranged with respect to a plane passing through the center that is common to said ring cores and is perpendicular to the central axis thereof;

coaxial cable means having first connections to said primary transformer and secondary transformer via a gap in said electrostatic shield means, for connecting said primary transformer and secondary transformer to a measurement instrument; and balance means coupled to said gap and said first connections for equalizing a potential at said first connections and a mean value of potentials at ends of said gap.

2. An electromagnetic induction-type probe in accordance with claim 1, wherein said balance means causes amplitudes of potentials of both ends of said gap to coincide, with mutually opposite phases with respect to a potential of an outer conductor of said coaxial cable means.

3. An electromagnetic induction-type probe in accordance with claim 2, wherein said balance means further comprises:
a transformer having a pair of terminals and a center tap, said center tap connected to said outer conductor of said coaxial cable means and said pair of terminals are connected, respectively, to said ends of said gap.

* * * * *